United States Patent
Bartley et al.

(10) Patent No.: US 7,045,488 B2
(45) Date of Patent: May 16, 2006

(54) CYLIC OLIGOMER TRACTION FLUID

(75) Inventors: Stuart L. Bartley, Wickliffe, OH (US); Douglas M. Barr, Belper (GB); Richard M. Lange, Euclid, OH (US); Craig D. Tipton, Perry, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 53 days.

(21) Appl. No.: 10/147,238

(22) Filed: May 16, 2002

(65) Prior Publication Data

US 2003/0216264 A1 Nov. 20, 2003

(51) Int. Cl.
*C10M 105/04* (2006.01)
*C07C 13/18* (2006.01)

(52) U.S. Cl. .............. 508/110; 585/20; 252/73
(58) Field of Classification Search ........... 585/20; 508/110; 252/73
See application file for complete search history.

(56) References Cited

U.S. PATENT DOCUMENTS

| 3,394,603 A | 7/1968 | Rounds ............ 74/200 |
| 3,440,894 A | 4/1969 | Hammann et al. ...... 74/200 |
| 3,966,624 A | 6/1976 | Duling et al. ........ 252/52 R |
| 4,046,703 A * | 9/1977 | Duling et al. .......... 252/73 |
| 4,329,529 A * | 5/1982 | Nambu ................. 585/20 |
| 4,424,400 A | 1/1984 | Hentschel et al. ....... 585/20 |
| 4,533,778 A | 8/1985 | Henderson et al. ....... 585/13 |
| 4,762,635 A | 8/1988 | Forbus ................ 252/73 |
| 4,922,047 A * | 5/1990 | Chen et al. ........... 585/12 |
| 5,043,497 A * | 8/1991 | Muraki et al. .......... 585/20 |
| 5,126,065 A * | 6/1992 | Tsubouchi et al. ...... 585/10 |
| 5,259,978 A * | 11/1993 | Yoshimura et al. ..... 252/73 |
| 5,344,582 A * | 9/1994 | Umemoto et al. ...... 508/110 |
| 5,489,721 A | 2/1996 | Sowerby et al. ....... 585/532 |
| 5,759,528 A | 6/1998 | Yamada et al. ........ 424/69 |
| 6,242,393 B1 | 6/2001 | Ishida et al. .......... 508/462 |
| 6,372,696 B1 | 4/2002 | Tipton ............... 508/110 |

FOREIGN PATENT DOCUMENTS

| EP | 0 281 060 | 9/1988 | ........ 169/4 |
| EP | 328 642 | 3/1993 | |
| EP | 842 974 | 5/1998 | |
| WO | WO 01/34738 | 5/2001 | |

OTHER PUBLICATIONS

Kuntz et al., Makromol, Chem., Macromol Symp. 13/14, pp 337–362, 1998.

* cited by examiner

*Primary Examiner*—Ellen M McAvoy
(74) *Attorney, Agent, or Firm*—David M. Shold; Michael F. Esposito

(57) ABSTRACT

Cyclic oligomers derivable from the copolymerization of isobutylene and isoprene can be hydrogenated to form 1-(2,2,4-trimethylpentyl)-2-isopropyl-3,3,5,5-tetramethylcyclohexane and related compounds, which are useful in lubricants such as a traction fluids.

23 Claims, No Drawings

CYLIC OLIGOMER TRACTION FLUID

BACKGROUND OF THE INVENTION

The present invention relates to a new composition comprising 1-(2,2,4-trimethylpentyl)-2-isopropyl-3,3,5,5-tetramethylcyclohexane and related compounds, and their use as a lubricant such as a traction fluid component.

Traction fluids of a variety of types and sources are known, many of them containing alicyclic molecules. For example, U.S. Pat. No. 4,533,778, Henderson et al, Aug. 6, 1985, discloses traction fluid lubricants derived from mineral oil, having a significant portion made up of multiring components of at least three rings. Varying amounts of 1-ring paraffins can also be present.

U.S. Pat. No. 3,440,894, Hammann et al., Apr. 29, 1969, discloses the use of certain cyclic and acyclic hydrocarbon-containing compound for tractive drives. Among various tractants reported is isodecylcyclohexane.

Kuntz et al., *Makromol. Chem., Macromol. Symp.* 13/14, pp 337–362, 1998, discloses cyclic oligomer formation in the copolymerization of isoprene with isobutylene, among them the (unsaturated) compound 1-isopropenyl-2,2,4,4-tetramethyl-6-(2,2,4-trimethylpentyl)-cyclohexane.

U.S. Pat. No. 3,394,603, Rounds, Jul. 30, 1968, discloses friction drive fluids including polymeric products of the $C_3$–$C_5$ olefin hydrocarbon monomers. The stability of the transmission oil is increased if the polymer is hydrogenated to remove unsaturation.

European Patent Publication 0 328 642 B, Mar. 3, 1993, discloses a traction fluid which includes the hydrogenation product of polyisobutylene, having a degree of polymerization n, of 6 to 200.

Many existing traction fluids, however, are very expensive and are deficient in traction coefficient and viscometrics (viscosity performance over a wide temperature range. The present invention provides an economical traction fluid or traction fluid component with good traction coefficient and viscometrics. The component can also be used in hydraulic fluids including farm tractor hydraulic fluid, automatic transmission fluid, fluids for push-belt and chain-type continuously variable transmission, and dual clutch transmissions.

SUMMARY OF THE INVENTION

The present invention provides a method for lubricating a mechanical power transmission apparatus, comprising supplying to said apparatus a fluid comprising a saturated alicyclic hydrocarbon composition comprising molecules containing 13 to 33 carbon atoms, said composition being prepared by the reaction of branched $C_4$ to $C_6$ ethylenically mono-unsaturated and di-unsaturated hydrocarbons in the presence of an acid catalyst, followed by hydrogenation.

In another aspect, the invention provides a method for lubricating a mechanical power transmission apparatus, comprising supplying to said apparatus a fluid comprising a saturated alicyclic hydrocarbon composition comprising molecules represented by the general structure [I]:

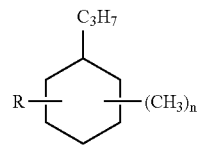

where n is 2 to 6 and R is hydrogen or a branched alkyl group containing 4 to 12 carbon atoms.

In yet an other aspect, the invention provides a lubricant comprising a saturated alicyclic hydrocarbon composition comprising molecules containing 13 to 33 carbon atoms, said composition being prepared by the reaction of branched $C_4$ to $C_6$ ethylenically unsaturated hydrocarbons in the presence of a Lewis acid, followed by hydrogenation; and at least one additive selected from the group consisting of viscosity modifiers, dispersants, detergents, antioxidants, and antiwear agents.

In yet another aspect, the invention provides a composition of matter comprising a saturated hydrocarbon represented by the structure [II]

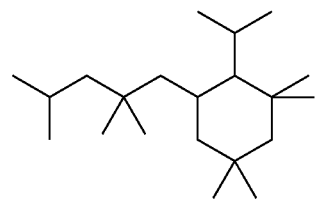

In yet another aspect, the invention provides a method for preparing a saturated alicyclic hydrocarbon having 13 to 33 carbon atoms, comprising reacting isobutylene and isoprene in the presence of an acid catalyst, thereby preparing an unsaturated alicyclic hydrocarbon, and hydrogenating the unsaturation thereof to provide said saturated alicyclic hydrocarbon.

DETAILED DESCRIPTION OF THE INVENTION

Various preferred features and embodiments will be described below by way of non-limiting illustration.

In one aspect, the present invention provides a method for lubricating a mechanical power transmission apparatus, comprising supplying to said apparatus a fluid comprising a saturated alicyclic hydrocarbon composition comprising molecules containing 13 to 33 carbon atoms, said composition being prepared by the reaction of branched $C_4$ to $C_6$ ethylenically mono-unsaturated and di-unsaturated hydrocarbons in the presence of an acid catalyst, followed by hydrogenation.

The mechanical power transmission apparatus in question can be any of a variety of transmission devices, including automotive transmissions such as automatic transmissions. A type of transmission device particularly envisioned is a traction drive. Traction drives are devices in which power or torque is transmitted from an input element to an output element through nominal point or line contact, typically with a rolling action, by virtue of the traction between the contacting elements. Traction drives can be generally used in automotive or industrial machinery for transmitting power between rotating members. They can be used as automatic transmissions and are particularly suitable as a form of continuously variable automatic transmission for use in automobile drivetrains and other applications.

While the working elements of a traction drive are sometimes spoken of as being in contact, it is generally accepted that a fluid film must be provided therebetween. Thus, rather than metal-to-metal rolling contact, a film of fluid is introduced into the load zone, and power is transmitted by shearing of the film, which may become very viscous due to the high pressure at the contact area. The nature and properties of the fluid, therefore, will determine to a large extent the performance and capacity of the traction drive. Traction fluids will preferably have a high shear resistance (often measured as "traction coefficient") to maximize the power transmission performance. Low viscosity, particularly at low temperatures, is also desirable for efficient operation under cold conditions. The fluid should ideally also exhibit good lubricating properties for and compatibility with other components of the traction drive. Such fluids also serve to remove heat and prevent wear at the contact surfaces and to lubricate bearings and other moving parts associated with the drive.

The saturated alicyclic hydrocarbon molecules which are a part of the present invention preferably contain 17 to 29 carbon atoms, and more preferably 17 to 25 carbon atoms. Most typically they contain 21 carbon atoms, as will be evident from the method of their production. However, variations in reaction conditions as well as variations in reactants can lead to mixtures of molecules containing differing numbers of carbon atoms, as will be apparent to the person skilled in the art.

The unsaturated precursors to the molecules of the present invention can be isolated as a fraction of the product obtained in the cationic copolymerization of isobutene (an example of a C-4 monoolefin) and isoprene (an example of a C-5 diolefin). Although both of these monomers are branched, a greater or lesser proportion of unbranched monomers can also be present, leading to a correspondingly greater or lesser proportion of the resulting molecules which have different, or reduced, amounts of branching. An example of an unbranched monoolefin is 1-butene; an example of an unbranched diolefin is 1,3-butadiene. Other examples of branched and unbranched mono- and diolefins of 4 to 6 carbon atoms include 2-butene, isopentene, 1-pentene, 2-pentene, 2-methyl-1-butene, 2-methyl-2-butene, 3-methyl-1-butene, 1-hexene, 2-hexene, 3-hexene, 2-methyl-1-pentene, 2-methyl-2-pentene, 3-methyl-1-pentene, 3-methyl-2-pentene, 2-ethyl-1-butene, 4-methyl-1-pentene, 4-methyl-2-pentene, 2,3-dimethyl-1-butene, 2,3-dimethyl-2-butene, 3,3-dimethyl-1-butene, 1,3-pentadiene, 1,4-pentadiene, 1,3-hexadiene, 1,4-hexadiene, 1,5-hexadiene, 2,4-hexadiene, 2-methyl-1,3-pentadiene, 2-methyl-1,4-pentadiene, 4-methyl-1,3-pentadiene, 3-methyl-1,3-pentadiene, 3-methyl-1,4-pentadiene, 2-ethyl-1,3-butadiene, and 2,3-dimethyl-1,3-butadiene. (In the foregoing list, those substances without named substituents or an iso-designation are, according to convention, the linear isomers.) The double bonds are preferably terminal. In the dienes, the two double bonds are preferably conjugated.

The preferred product used in the present invention preferably comprises 4 molar portions of the monoolefin and 1 molar portion of the diolefin. Accordingly, the molar ratio of monoolefin to diolefin which is reacted or supplied to the reaction mixture is preferably about 4:1, that is with a molar excess of the monoolefin, in a broad ratio of 2:1 to 20:1, preferably 3:1 to 10:1.

The monomers are reacted in the presence of an acid catalyst, for example, a Lewis acid catalyst of the type that is well known for use in acid-catalyzed polymerization of olefins. A Lewis acid catalyst is a molecule or ion that can combine with another molecule or ion by forming a covalent bond with two electrons from the second molecule or ion. Specific examples of Lewis acid catalysts include $BF_3$ and aluminum halides such as $AlCl_3$, $AlClBr_2$, $AlBr_3$, and $AlBrCl_2$. These and catalysts, as well as typical conditions for polymerization of olefins, are described in U.S. Pat. No. 5,489,721 and in the above-referenced Makromol. Chem. article by Kuntz et al.

The reaction can occur in the presence of an inert medium such as a hydrocarbon medium in which the reactants are soluble, e.g., a mixture of isobutane and hexanes. The temperature of reaction is not particularly critical; temperatures of 0° C. to room temperature, i.e., 25° C. can be used, for instance, or, in one example, a temperature of about 5° C. Atmospheric or supra-atmospheric pressures can be used, as appropriate. The reaction can be conducted batchwise, continuously, or semicontinuously; typically a continuously-stirred tank reactor is employed. The desired cyclic oligomers are separated from the crude reaction mixture by known methods such as washing, drying, and evaporation of solvent. Conventional isolation processes may provide a mixture of cyclic oligomers and polymer. The cyclic oligomers can be removed from the polymer by stripping under high vacuum (e.g., 13 to 1330 Pa [0.1 to 10 mm Hg]) at elevated temperatures (e.g., 100–250° C.). The preferred C-21 oligomer can be separated from other oligomers (e.g., the C-13) by fractional distillation under vacuum. If fractional distillation or other separation is not conducted, a mixture of oligomers, ranging in carbon number from 13 to 33, especially 17 to 29 or to 25, can be obtained and can be profitably used.

The initially isolated oligomers will typically contain residual unsaturation, such as a terminal ethylenic double bond in the isopropylene substituent on the cyclohexane ring in structure [II]. It is desired that this unsaturation in the oligomer be largely or completely removed by hydrogenation, either before or (preferably) after separation of the oligomer, and before the oligomer is put to use in a fluid application. Hydrogenation can be effected by any of the conventional methods for reducing hydrocarbons, including treatment with elemental hydrogen, optionally under pressure and at elevated temperature over a metal catalyst. In one embodiment, the catalyst is nickel on a support such as Kieselguhr. Such catalysts are well known and are commercially available. The re-suiting hydrogenated product is isolated by conventional methods.

The resulting materials can be represented by the general Structure I:

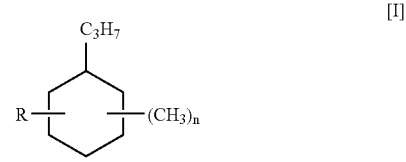

[I]

or, in a specific embodiment, by the more specific Structure II:

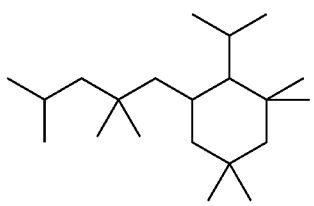
[II]

In Structure I, n is 2 to 6, preferably 3 to 5, and more preferably 4. A preferred disposition of the methyl groups is in the 3 and 5 position on the ring as shown in Structure II; moreover, preferably at least two of the methyl groups are attached geminally to a carbon atom. R is hydrogen or a branched alkyl group containing 4 to 12 carbon atoms, preferably 6 to 10 carbon atoms, and more preferably 8 carbon atoms. It is preferably attached to the 6-membered ring at a position vicinal to the $C_3H_7$ (isopropyl) group. If additional monomers are incorporated into the molecule, the length of the R group can be proportionally greater; for instance, it can be a C-16 group if the total number of carbon atoms in the molecule is 33. Similarly, the length of the R group can be proportionally less; for instance, it can be a C-4 group if the number of carbon atoms in the molecule is 17. Such variation will typically result from a different number of monomers being incorporated into the resulting molecule. A preferred R group is the 2,2,4-trimethylpentyl group shown in Structure II. A preferred material is 1-(2,2,4-trimethylpentyl)-2-isopropyl-3,3,5,5-tetramethylcyclohexane.

The C-13 product can likewise be separated by fractional distillation. This material is believed to have the structure [IV]:

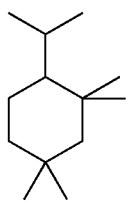
[IV]

This material will have a higher volatility than the C-21 oligomer; it will be useful in applications which are relatively insensitive to volatility or in admixture with the C-21 oligomer. The C-13 product may also be blended with other traction fluids to reduce the low temperature viscosity, while retaining a high traction coefficient. The C-13 product may also be present in admixture with small amounts of other materials in the C-8 to C-16 range.

The above-described hydrocarbons exhibit attractive properties for use in a traction fluid, either alone or with other fluid components. While any of a variety of other fluid components may be used for various purposes (such as various natural or synthetic oils of lubricating viscosity), for preparation of a high quality traction fluid, the other fluid components will typically be other materials known to be used as traction fluids. These include polymers or oligomers of at least one olefin containing 3 to 5 carbon atoms; and hydrocarbon or ester molecules containing non-aromatic cyclic moieties, and mixtures thereof. Such traction fluids are well known and are described in greater detail in PCT Patent Application WO 01/34738 and in the references cited therein. A particularly useful traction fluid which can be mixed with or added to the compound of the present invention comprises a predominantly linear (as opposed to cyclic) hydrogenated dimer of alpha-alkylstyrene. This material can be represented by the general structure [III]

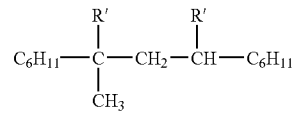
[III]

wherein each R' is an alkyl group of 1 to 4 carbon atoms and $C_6H_{11}$ represents a cyclohexyl group. Such materials and their preparation are described in detail in U.S. Pat. No. 3,975,278.

The amount of such additional traction fluid which is typically employed is such that the weight ratio of the saturated alicyclic hydrocarbon composition of the present invention to the additional traction fluid (such as the Santotrak™20) is broadly 5:95 to 90:10, preferably 10:90 to 50:50, alternatively, 15:85 to 45:55, or 20:80 to 40:60, or 25:75 to 35:65, or about 30:70. That is, in certain embodiments the amount of the additional traction fluid can equal or exceed the amount of the saturated alicyclic hydrocarbon of the present invention. The presence of the additional traction fluid can be desirable in order to modify the viscosity, traction coefficient, volatility, antiwear, or other physical properties of the composition.

The fluid which is prepared by the mixture of components should preferably have a viscosity of greater than 2.5 mm²/s (2.5 cSt) at 100° C. (ASTM D-445), and more preferably a viscosity of at least 3.0 mm²/s (3.0 cSt) or 3.5 mm²/s (3.5 cSt), typically up to 8.0 mm²/s (8.0 cSt) or 7.0 mm²/s (7.0 cSt) or 6.0 mm²/s (6.0 cSt) at 100° C.

In order to formulate a commercially useful traction fluid, there will optionally and typically be a number of additional additives present. Among these can be dispersants, detergents, viscosity modifiers, phosphorus compounds, antiwear agents, antioxidants, and low temperature viscosity control agents. These materials and their preparation are described in greater detail in PCT Patent Application WO 01/34738 and in the references cited therein.

The dispersants useful as a component in the present fluids include acylated amines, carboxylic esters, Mannich reaction products, hydrocarbyl substituted amines, and mixtures thereof.

Acylated amine dispersants include reaction products of one or more carboxylic acylating agent and one or more amine. Hydrocarbyl-substituted maleic acylating agents are the preferred unsaturated acylating agent. The procedures for preparing the acylating agents are well known to those skilled in the art and have been described for example in U.S. Pat. No. 3,412,111. The amines which react with the acylating agents may be known amines, preferably a polyamine, such as an alkylenepolyamine or a condensed polyamine. Polyamines can be aliphatic, cycloaliphatic, heterocyclic or aromatic. Examples of the polyamines include alkylene polyamines, hydroxy containing polyamines, arylpolyamines, and heterocyclic polyamines.

Carboxylic ester dispersants can be prepared by reacting at least one or more carboxylic acylating agents, preferably a hydrocarbyl substituted carboxylic acylating agent, with at least one organic hydroxy compound and optionally an amine. The hydroxy compound may be an alcohol or a hydroxy containing amine.

In another embodiment, the dispersant can be a hydrocarbyl-substituted amine. These hydrocarbyl-substituted amines are well known to those skilled in the art. Typically, hydrocarbyl substituted amines are prepared by reacting olefins and olefin polymers, including the above polyalkenes and halogenated derivatives thereof, with amines (mono- or polyamines).

In another embodiment, the dispersant can be a Mannich dispersant. Mannich dispersants are generally formed by the reaction of at least one aldehyde, such as formaldehyde and paraformaldehyde, at least one amine, preferably a polyamine, such as a polyalkylenepolyamine, and at least one alkyl substituted hydroxyaromatic compound.

The dispersant can also be a dispersant which has been treated or reacted with any of a variety of common agents. That is, they can be borated dispersants or sulfurized dispersants.

The amount of the dispersant in the traction fluid composition, if present, is preferably 1 to 10 weight percent, preferably 1.5 to 7 weight percent, and more preferably 2 to 3 weight percent.

The additive component for the traction fluid can also contain one or more detergents, which are normally salts, and specifically overbased salts. Overbased salts, or overbased materials, are single phase, homogeneous Newtonian systems characterized by a metal content in excess of that which would be present according to the stoichiometry of the metal and the particular acidic organic compound reacted with the metal.

The overbased materials are prepared by reacting an acidic material (typically an inorganic acid or lower carboxylic acid, preferably carbon dioxide) with a mixture comprising an acidic organic compound, a reaction medium comprising at least one inert, organic solvent (such as mineral oil, naphtha, toluene, xylene) for said acidic organic material, a stoichiometric excess of a metal base, and a promoter.

The acidic organic compounds useful in making the overbased compositions of the present invention include carboxylic acids, sulfonic acids, phosphorus-containing acids, phenols or mixtures thereof. Preferably, the acidic organic compounds are carboxylic acids or sulfonic acids with sulfonic or thiosulfonic acids (such as hydrocarbyl-substituted benzenesulfonic acids) and hydrocarbyl-substituted salicylic acids more preferred.

The metal compounds useful in making the overbased salts are generally any Group 1 or Group 2 metal compounds (CAS version of the Periodic Table of the Elements). The Group 1 metals of the metal compound include Group 1a alkali metals (e.g., sodium, potassium, lithium) as well as Group 1b metals such as copper. The Group 1 metals are preferably sodium, potassium, lithium and copper, more preferably sodium or potassium, and more preferably sodium. The Group 2 metals of the metal base include the Group 2a alkaline earth metals (e.g., magnesium, calcium, barium) as well as the Group 2b metals such as zinc or cadmium. Preferably the Group 2 metals are magnesium, calcium, barium, or zinc, preferably magnesium or calcium, more preferably calcium.

The amount of the overbased material, that is, the detergent, if present, is preferably 0.05 to 5 percent by weight of the composition, more preferably 0.05 to 3 percent, 0.1 to 1.5 percent, or most preferably 0.2 to 1 percent by weight.

Both a dispersant and a detergent can be included in the composition. For example, a succinimide dispersant and a calcium overbased sulfonate detergent can be used.

The compositions of the present invention can also contain a viscosity index modifier, typically a polymeric viscosity index modifier, preferably in limited amounts, that is, up to 10 percent by weight of the composition. Preferably the amount of this component is 0 to 3 percent by weight, and in one embodiment the traction fluids are substantially free from polymeric viscosity index modifiers.

Polymeric viscosity index modifiers (VMs) are extremely well known in the art and most are commercially available. Hydrocarbon VMs include polybutenes, poly(ethylene/propylene) copolymers, isobutylene/isoprene copolymers, optionally hydrogenated, and hydrogenated polymers of styrene with butadiene or isoprene. Ester VMs include esters of styrene/maleic anhydride polymers, esters of styrene/maleic anhydride/acrylate or methacrylate ter-polymers, and polymethacrylates. Dispersant viscosity modifiers based on any of the foregoing polymers, modified to impart dispersant functionality, are also useful. The polymethacrylates are available from RohMax and from The Lubrizol Corporation; polybutenes from Ethyl Corporation, BASF, and Lubrizol; ethylene/propylene copolymers from ExxonMobil and ChevronTexaco; hydrogenated polystyrene/isoprene polymers from Shell; styrene/maleic esters from Lubrizol, and hydrogenated styrene/butadiene polymers from BASF.

Another optional component of the traction fluids of the present invention is a phosphorus compound such as a phosphorus acid, a phosphorus acid salt, a phosphorus ester, or mixtures thereof. The phosphorus acid or ester can be of the formula $(R^1X)(R^2X)P(X)_nX_mR^3$ or a salt thereof, where each X is independently an oxygen atom or a sulfur atom, n is 0 or 1, m is 0 or 1, m+n is 1 or 2, and $R^1$, $R^2$, and $R^3$ are hydrogen or hydrocarbyl groups, and preferably at least one of $R^1$, $R^2$, or $R^3$ is hydrogen. These R groups can be, specifically, alkyl, phenyl, or alkylphenyl groups. This component thus includes phosphorous and phosphoric acids, thiophosphorous and thiophosphoric acids, as well as phosphite esters, phosphate esters, thiophosphite esters, and thiophosphate esters. Phosphoric acid and phosphorous acid are well-known items of commerce. Thiophosphoric acids and thiophosphorous acids are likewise well known and are prepared by reaction of phosphorus compounds with elemental sulfur or other sulfur sources.

The amount of the above phosphorus acid, salt, or ester in the traction fluid of the present invention, if present, is preferably an amount sufficient to provide at least 0.01 percent by weight of phosphorus to the fluids (calculated as P), preferably 0.01 to 0.1 percent, and more preferably 0.03 to 0.06 or 0.05 percent by weight.

Another optional species in the traction fluids of the present invention is a friction modifier. Friction modifiers include alkoxylated fatty amines, borated fatty epoxides, fatty phosphites, fatty epoxides, fatty amines, borated alkoxylated fatty amines, metal salts of fatty acids, fatty acid amides, glycerol esters, borated glycerol esters, and condensation products of fatty acids and polyamines, including fatty imidazolines. One such material is the condensation product of isostearic acid and diethylene triamine.

One preferred example of a friction modifier, zinc salts of fatty acids are well known materials. A preferred acid is oleic acid, and the correspondingly preferred salt is zinc oleate, a commercially available material, the preparation of which is well known and is within the abilities of the person skilled in the art. Slightly basic forms of zinc oleate, represented for example by $Zn_4Oleate_6O_1$, are also useful.

Condensation products of a carboxylic acid with a 1,2 diaminoethane compound are also useful friction modifiers, as are borated epoxides (actually, borate esters), diethoxylated long chain amines, and certain phosphorus-containing materials.

The amount of friction modifier, if present, is preferably 0.01 to 2 percent by weight of the traction fluid composition. More preferably it is 0.05 to 1.2 percent, and most preferably 0.1 to 1 percent by weight.

Antioxidants (that is, oxidation inhibitors), including hindered phenolic antioxidants such as 2,6-di-t-butylphenol, secondary aromatic amine antioxidants such as dialkyl (e.g., dinonyl) diphenylamine, sulfurized phenolic antioxidants, oil-soluble copper compounds, phosphorus-containing antioxidants, molybdenum compounds such as the Mo dithiocarbamates, organic sulfides, disulfides, and polysulfides. An extensive list of antioxidants is found in U.S. Pat. No. 6,251,840.

The optional low-temperature viscosity control agent (which is to be distinguished from a viscosity index modifier, another optional component described above), which is desirable in certain prior formulations, can often be eliminated entirely from the traction fluids of the present invention, since the present cyclic oligomer inherently has excellent low temperature viscosity properties. However, if an additional low-temperature viscosity control agent is desired, it can be selected from among a variety of materials which are known to be useful for this purpose, including (a) oligomers or polymers of linear alpha olefins of at least 8 carbon atoms, (b) naphthenic oils, (c) synthetic ester oils, (d) polyether oils, and mixtures thereof. These materials are distinguishable from the base fluids, described above, in that they are generally lower viscosity materials than the base fluids, typically exhibiting a viscosity of up to or less than 2.5 $mm^2/s$ (2.5 cSt), preferably 1.5 to 2.5, or 1.8 to 2.3 $mm^2/s$ (1.5 to 2.5 or 1.8 to 2.3 cSt) at 100° C. These are also materials which typically retain a measure of mobility at low temperatures (e.g., −40° C.) and can serve to reduce the low temperature viscosity of fluids to which they are added. Materials which are of unduly high viscosity or which do not retain mobility at low temperatures do not effectively serve as low-temperature viscosity control agents. Determination of viscosity and low temperature mobility is well within the abilities of those skilled in the art. These materials are described in greater detail in PCT Patent Publication WO 01/34738.

The amount of the low temperature viscosity control agent in the traction fluid, if present, can be 1 to 20 percent by weight of the traction fluid, or 3 to 15, or 5 to 10 percent by weight.

Other materials which are commonly used in transmission fluids, such as seal swell agents, corrosion inhibitors, dyes, and foam inhibitors, can also be used.

The compounds and compositions of the present invention can be used in traction power transmission devices, as described above. They can also be used in other applications as gear oils, automatic transmission fluid, including continuously variable transmission fluid, manual transmission fluids (particularly for lubricating a synchronizer in a manual transmission), dual clutch transmission fluid, hydraulic fluids, and other fluids for use in applications for which an increase in coefficient of friction under pressure is desired.

The cyclic compounds of the present invention, besides possessing excellent frictional properties, exhibit extremely good low temperature properties. Compositions based on the present cyclic oligomers can be formulated to exhibit Brookfield viscosities of 15 Pa-s, 10 Pa-s, 5 Pa-s (15,000, 10,000, or 5,000 cP) or even lower at −30° C., while still maintaining good traction performance.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic sites of other molecules. The products formed thereby, including the products formed upon employing the composition of the present invention in its intended use, may not susceptible of easy description. Nevertheless, all such modifications and reaction products are included within the scope of the present invention; the present invention encompasses the composition prepared by admixing the components described above.

EXAMPLES

Example 1

Isolation and purification of cyclic oligomers. Cyclic oligomers are isolated from an isobutylene/isoprene copolymerization reaction. The reaction is carried out at 5° C. in a solvent mixture of isobutane and hexanes and a catalyst of $AlCl_3$. The mole ratio of the starting materials isobutylene and isoprene is 10:1. The crude product mixture is washed several times with water; the organic layers are separated, combined, dried with $MgSO_4$, and filtered. Hexanes are removed by evaporation to give a mixture of polymer and cyclic oligomers. This mixture contains about 10 to 12% by weight of cyclic oligomers, approximately 7 to 9 percent being the C-21 oligomer, as determined by gas chromatography and $^1$H-NMR.

The cyclic oligomer product mixture is separated from the polymer by deep stripping at 200° C. and 130 Pa (1 mm Hg) for about 2 hours. The crude cyclic oligomer mixture is then fractionally distilled under vacuum using a 25–30 mm vigreux column. The low boiling components are first separated and the C-21 oligomer is distilled at 13 Pa (0.1 mm Hg) and 100° C. head temperature. Under these conditions the separation of the C-13 oligomer from the C-21 oligomer is excellent. The identity and purity of the fractions are determined by NMR and gas chromatography-mass spectroscopy.

The C-21 fraction as initially isolated is an alkene. It is reduced to the alkane of Structure I, above, by subjecting it to hydrogen at 4.1 MPa (600 psi) at 155° C. for 6 hours using a catalyst of nickel on kieselguhr. The resulting product is isolated by filtration. The identity of the product is determined by gc-mass spec, $^1$H-NMR, and 2D-$^{13}$C NMR.

Examples 2–6

Preparation and properties of cyclic oligomer and blends. The C-21 cyclic oligomer of the present invention, as well as various blends shown in the table below, were evaluated as to high and low temperature viscosity (kinematic viscosity at 100° C., in mm²/sec (cSt) and Brookfield viscosity at −30° C., in Pa-s ($10^{-3}$ cP)) as well as traction performance. A variety of commercial traction fluids are is included in the table for comparison. The traction coefficient is evaluated at a slide-to-roll ratio of 0 to about 10 at 2.5 m/s, 100° C., and 1.25 GPa pressure, using the technique more fully set forth in PCT Patent Publication WO 01/34738. In Examples 2, 3, 4, and 5, an additive package is included; in examples 6, 7, 8, and 9, the cyclic oligomer or reference fluid (alone) is tested without the additives. (The commercial fluids of Examples 8 and 9 may contain their own additives, not accounted for here.) The additive package, when used, comprises about 6.8% by weight of the formulations tested, and includes the following components, in approximate percentages by weight:

- 35.5 methacrylate copolymer viscosity modifier
- 29.8 mineral oil
- 12.7 borated & non-borated succinimide dispersant(s)
- 9.7 antioxidants and inhibitors
- 5.2 Ca sulfonate and salicylate detergent(s)
- 2.9 seal swell agent
- 2.0 dialkyl hydrogen phosphite(s)
- 1.8 friction modifier(s)
- 0.3 phosphoric acid (85%)
- smaller amounts of other conventional additives

| Ex. | Fluid | viscosity at 100° C. (mm²/s) | viscosity at −30° C. (Pa-s) | Traction Coefficient (at slide/roll ratio) 100° C., 125 GPa |
|---|---|---|---|---|
| 2 | Cyclic oligomer of Ex. 1 (with additives) | 4.03 | 4.37 | —[a] |
| 3 | Ex. 1 + fluid of structure (III) (50:50) (with additives) | 4.03 | 10.4 | —[a] |
| 4 | Ex. 1 + fluid of structure (III) (30:70) (with additives) | 4.16 | 15.4 | 0.084 (2.5%) 0.088 (5.0%) 0.089 (7.5%) 0.090 (10%) |
| 5* | Fluid of structure (III) (with additives) | 4.46 | 38 | 0.090 (2.5%) 0.094 (5.0%) 0.095 (7.5%) 0.095 (10%) |
| 6 | Cyclic oligomer of Ex. 1 (alone) | 2.8 | 3.55 | —[a] |
| 7* | Fluid of structure (III) (alone) | 3.51 | 33 | 0.094 (2.5%) 0.097 (5.0%) 0.098 (7.5%) 0.099 (10%) |
| 8* | Santotrac ™ 50[b] (alone) | 5.5 | 36 | 0.090 (2.5%) 0.093 (5.0%) 0.094 (7.5%) 0.095 (10%) |
| 9* | KTF-1 ™[c] (alone) | 5.26 | 23 | 0.087 (2.5%) 0.090 (5.0%) 0.091 (7.5%) 0.093 (10%) |

[a]Not measured because scarring of the test specimen occurred with these samples.
[b]Commercial traction fluid from Findett Corporation
[c]Commercial traction fluid from IKK
*Reference Examples The results show that the cyclic oligomer of the present invention has substantially the same high temperature viscosity as that of the reference fluids but it has dramatically decreased low temperature viscosity, not only as a neat fluid, but also in blends. As a result, traction fluids with greatly improved low temperature performance can be formulated using the oligomer of the present invention. The blend of Example 4 also exhibited very good traction coefficient performance. The formulations corresponding to Examples 2, 3, and 6 will show similarly good traction performance when formulated with a combination of additives suitably designed for the particular base fluid.

Example 10

Example 4 is repeated except that in place of the C-21 cyclic oligomer of Example 1, the same amount of the C-13 cyclic oligomer of structure IV above is used.

Example 11

Example 1 is repeated except the entire content of the mixed oligomers from the stripping step is hydrogenated, under similar conditions, to provide a traction fluid having a broader distribution of components.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A method for lubricating a mechanical power transmission apparatus, comprising supplying to said apparatus a fluid comprising a saturated alicyclic hydrocarbon composition comprising molecules containing about 13 to about 33 carbon atoms and containing a ring having at least two geminal methyl groups, said composition being prepared by the reaction of branched $C_4$ to $C_6$ ethylenically mono-unsaturated and di-unsaturated hydrocarbons in the presence of an acid catalyst, followed by hydrogenation.

2. The method of claim 1 wherein said saturated alicyclic hydrocarbon composition comprises molecules containing predominantly 21 carbon atoms, said composition being produced as a fraction of the product obtained in the polymerization of isobutene and of isoprene, followed by hydrogenation.

3. The method of claim 1 wherein said saturated alicyclic hydrocarbon composition comprises molecules containing about 13 carbon atoms, said composition being produced as a fraction of the product obtained in the polymerization of isobutene and of isoprene, followed by hydrogenation.

4. The method of claim 1 wherein said saturated alicyclic hydrocarbon is represented by the general structure

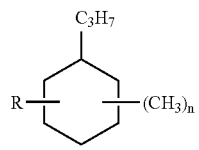

where n is 2 to about 6 and R is hydrogen or a branched alkyl group containing about 4 to about 12 carbon atoms.

5. The method of claim 4 wherein said saturated alicyclic hydrocarbon is represented by the structure

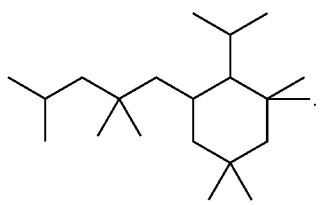

6. The method of claim 1 wherein said fluid further comprises at least one additive selected from the group consisting of viscosity modifiers, dispersants, detergents, antioxidants, and anti-wear agents.

7. The method of claim 1 wherein said fluid further comprises at least one additional base fluid component, other than a saturated alicyclic hydrocarbon comprising molecules containing about 13 to about 33 carbon atoms.

8. The method of claim 1 wherein the additional base fluid component is selected from the group consisting of polymers or oligomers of at least one olefin which contains 3 to about 5 carbon atoms, hydrocarbon or ester molecules containing non-aromatic cyclic moieties, and mixtures thereof.

9. The method of claim 7 wherein the additional base fluid component is a hydrogenated dimer of alpha-alkylstyrene.

10. The method of claim 9 where the saturated alicyclic hydrocarbon composition comprising molecules containing about 13 to about 33 carbon atoms and the hydrogenated dimer of alpha-alkylstyrene are present in relative weight ratios of about 10:90 to about 50:50.

11. A method for lubricating a mechanical power transmission apparatus, comprising supplying to said apparatus a fluid comprising a saturated alicyclic hydrocarbon composition comprising molecules represented by the general structure

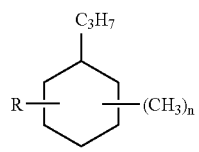

where n is 2 to about 6 and R hydrogen or is a branched alkyl group containing about 4 to about 12 carbon atoms, said molecules containing at least two geminal methyl groups on the ring.

12. A lubricant comprising a saturated alicyclic hydrocarbon composition comprising molecules containing about 13 to about 33 carbon atoms and containing a ring having at least two geminal methyl groups, said composition being prepared by the reaction of branched $C_4$ to $C_6$ ethylenically unsaturated hydrocarbons in the presence of a Lewis acid, followed by hydrogenation; and at least one additive selected from the group consisting of viscosity modifiers, dispersants, detergents, antioxidants, and anti-wear agents.

13. The lubricant of claim 12 wherein said saturated alicyclic hydrocarbon composition comprises molecules predominantly containing 21 carbon atoms, said composition being prepared by hydrogenation of a fraction of the product obtained in the polymerization of isobutene and isoprene.

14. The lubricant of claim 12 wherein said saturated alicyclic hydrocarbon is represented by the general structure

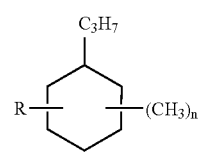

where n is 2 to about 6 and R is hydrogen or a branched alkyl group containing about 4 to about 12 carbon atoms.

15. The lubricant of claim 14 wherein said saturated alicyclic hydrocarbon is represented by the structure

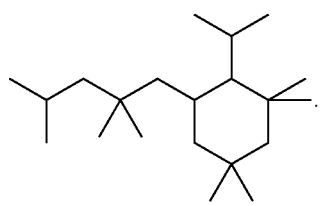

16. The lubricant of claim 12 further comprising at least one additional traction fluid component, other than a saturated alicyclic hydrocarbon comprising molecules containing about 13 to about 33 carbon atoms.

17. A lubricant comprising an alicyclic hydrocarbon composition comprising molecules represented by the general structure

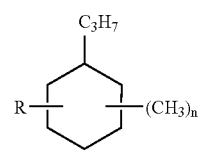

where n is 2 to about 6 and R is hydrogen or a branched alkyl group containing about 4 to about 12 carbon atoms, said molecules containing at least two geminal methyl groups on the ring; and at least one additive selected from the group consisting of viscosity modifiers, dispersants, detergents, antioxidants, and anti-wear agents.

18. The lubricant of claim 17 wherein the R group is attached to the 6-membered ring at a position vicinal to the $C_3H_7$ group.

19. The lubricant prepared by admixing the components of claim 12.

20. A composition of matter comprising a saturated hydrocarbon represented by the structure

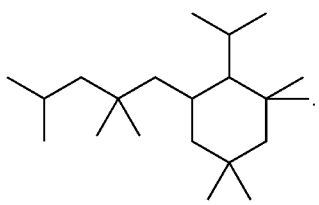

21. A method for preparing a saturated alicyclic hydrocarbon having about 13 to about 33 carbon atoms, comprising reacting isobutylene and isoprene in the presence of an acid catalyst, thereby preparing an unsaturated alicyclic hydrocarbon, and hydrogenating the unsaturation thereof to provide said saturated alicyclic hydrocarbon.

22. The method of claim 21 wherein said unsaturated alicyclic hydrocarbon is separated from the reaction mixture prior to hydrogenation.

23. The method of claim 21 wherein said unsaturated alicyclic hydrocarbon is represented by the structure

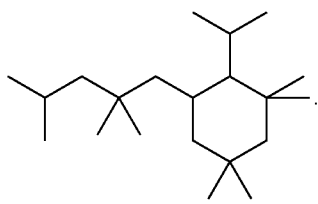

* * * * *

UNITED STATES PATENT AND TRADEMARK OFFICE
CERTIFICATE OF CORRECTION

| | | |
|---|---|---|
| PATENT NO. | : 7,045,488 B2 | Page 1 of 1 |
| APPLICATION NO. | : 10/147238 | |
| DATED | : May 16, 2006 | |
| INVENTOR(S) | : Bartley et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (53) days Delete the phrase "by 53 days" and insert -- by 641 days--

Signed and Sealed this

Twenty-second Day of May, 2007

JON W. DUDAS
*Director of the United States Patent and Trademark Office*